United States Patent [19]

Hargrove et al.

[11] Patent Number: 4,699,356
[45] Date of Patent: Oct. 13, 1987

[54] SAMPLING VALVE

[76] Inventors: Barry C. Hargrove, 8300 NW. 38 Terr., Bethany, Okla. 73008; James D. Madden, 428 Hanging Elm, Norman, Okla. 73069

[21] Appl. No.: 874,321
[22] Filed: Jun. 13, 1986
[51] Int. Cl.⁴ ............................................ F16L 37/28
[52] U.S. Cl. .............................. 251/149.6; 251/149.1; 137/329.1
[58] Field of Search .................. 251/149.4, 149.6; 137/329.1

[56] References Cited

U.S. PATENT DOCUMENTS 3,567,255  3/1971  Evans ................................. 251/149.6
4,354,523 10/1982  Hochmuth et al. ............... 251/149.6
4,476,892 10/1984  Boyce ................................ 251/149.6
4,509,554  4/1985  Failla ............................... 137/329.1

FOREIGN PATENT DOCUMENTS 2532220  2/1977  Fed. Rep. of Germany ... 251/149.4

Primary Examiner—A. Michael Chambers
Attorney, Agent, or Firm—Charles E. Krukiel; Thomas E. Kelley

[57] ABSTRACT

Fluid sampling valves having a central bore between an inlet and an outlet with a cylindrical valve stem having a conically-faced head which provides means for fluid sealing within the bore. Such valves are especially useful for sampling critical fluid systems such as aerospace hydraulic systems.

4 Claims, 2 Drawing Figures

SAMPLING VALVESAMPLING VALVE

This invention relates to a sampling valve for drawing fluids from contained systems. More particularly this invention relates to a sampling valve for drawing fluid from critical performing systems where failure of a component, such as the sampling valve, could result in severe consequences.

The sampling valve of this invention is particularly useful in aircraft hydraulic systems. Such systems actuate flight control surfaces, landing gear, brakes, windshield wipers, fire control equipment, armament systems and other vital units in both military and commercial aircraft. Such systems are complex and often utilize hundreds of meters of hydraulic lines often in redundant systems. Because of weight limitations the working volume of hydraulic fluids is desirably reduced to a minimum. Consequently the tolerance for leakage is frequently low.

Moreover, service operating conditions have become more severe as aircraft now fly higher and faster placing more extreme conditions, e.g., temperature, on hydraulic systems Advancing aircraft performance demands more and more power from hydraulic systems, for instance for actuating control surfaces. This factor, together with miniaturization, results in higher system temperatures and places emphasis on precision engineered components of lightweight design with very small clearances. As a result aircraft hydraulic fluids are required to maintain their properties within specifications without degradation, e.g., to products that induce erosion of fluid control surfaces having critical tolerances, while operating under more severe conditions. To assure that hydraulic fluids are maintained within specification parameters it would be useful to periodically sample hydraulic systems. Such sampling has heretofore not been convenient for lack of sampling valves meeting critical performance criteria required of aerospace equipment. What has been required is a small, lightweight, simple fail-safe fluid sampling valve capable of operating in high pressure over extended periods of time systems with negligible possibility of fluid loss.

There have been many attempts to provide such a valve, all of which have failed to find general acceptance by the aerospace industry. For instance Taylor in U.S. Pat., 3,794,289, incorporated herein by reference, discloses a "probe receiving plug" capable of functioning as a fluid sampling valve in the general manner of the valve according to this invention. A disadvantage of such a valve is that it utilizes an elongated valve stem with a ball-shaped head which is biased against a resilient O-ring. In the event of O-ring failure the ball shaped head would come in contact with a valve seat comprising a circular bore in a surface normal to the axis of motion of the valve stem. In order to provide an optimal sealing contact with negligible leakage it is necessary for the circular periphery of the valve seat to contact a matching circular surface on the ball terminating the stem. Such contacting is, however, most frequently extremely difficult to affect in practice.

Other examples of fluid sampling valves are disclosed in U.S. Pats. 4,484,482; 4,524,811; 4,537,219; 4,549,440; and 4,570,685.

SUMMARY OF THE INVENTION

It is an object of this invention to provide a fluid sampling valve suitable for use in aerospace hydraulic systems. It is another object of this invention to provide such a valve capable of being fabricated in a small, lightweight configuration. Another object of this invention is to provide such a valve utilizing simple mechanical principles. Another object of this invention is to provide a valve capable of fail-safe operation with negligible loss of fluid.

The above and other objects are accomplished by providing a fluid sampling valve which has, as a means for providing a fluid seal, a valve stem having a conically-faced head.

DETAILED DESCRIPTION OF THE DRAWINGS

Figure 1:
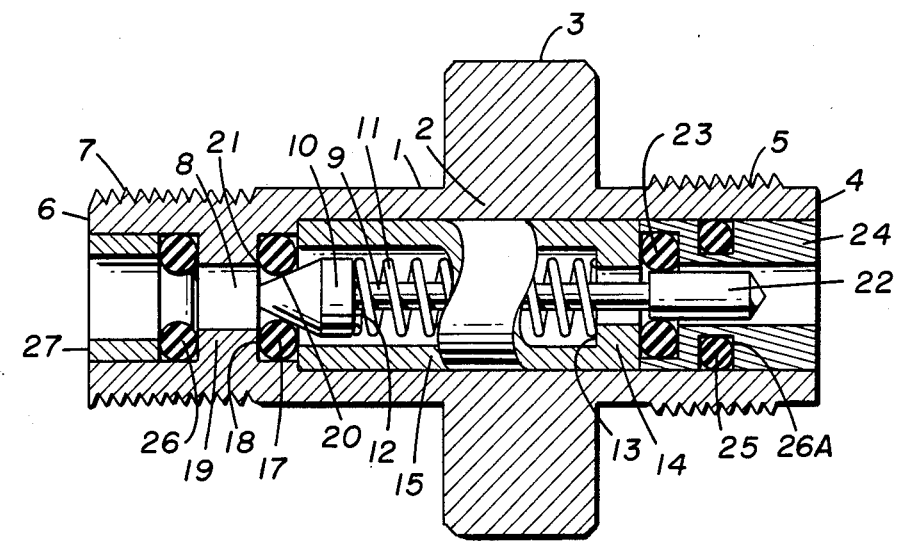
FIGS. 1 and 2 are cross-sectional illustrations of valves according to this invention.

In FIG. 1 there is shown in cross sectional view, one embodiment of the valve of this invention. Valve 1 comprises a body 2 fabricated from a metal of substantial strength, e.g. steel, stainless steel, etc. The body is generally of cylindrical shape which is convenient for providing a design capable of withstanding high internal pressure. The valve body optionally has a hexagonally-shaped central section 3 to facilitate installation, for instance with socket drives. The body has a vessel end 4 which is adapted to be connected to a fluid-containing vessel, for instance by external threads 5 or other common means.

The body also has a sample end 6 which is adapted to be removably sealed with a cap, (not shown) for instance by utilizing external threads 7 or other common means for securing caps. In this regard it is generally preferred that the sample end be sealed with a threaded cap of sufficient structural strength to retain hydraulic fluid within the sample valve in the unlikely, albeit not impossible, event of total failure of the valve sealing mechanisms. A convenient way of assisting in such sealing is to provide the interface of the cap with a full face gasket that can sealingly engage the outer surfaces of sample end 6. Such a cap also provides a convenient means of avoiding the deposition of dirt or other foreign material within the sample end of the valve thereby minimizing the possibility of inadvertent contamination of a fluid sample being withdrawn from the valve and ensuring high reliability of analysis of fluid samples withdrawn from the valve.

Within the body of the valve there is a central bore 8 interconnecting sample end 6 and vessel end 4 thereby allowing fluid communication through the valve. The central bore is generally aligned along a central access. The shape of the bore is generally circular in cross section and of variable diameter to accommodate a variety of functional parts within the valve.

Within the central bore there is a cylindrical valve stem 9 which is elongated along the central access of the bore. At one end of the stem proximate to the sample end 6 of the valve there is a conically-faced head 10. The valve stem is urged toward the sample end of the valve by biasing means, for instance spring 11 exerting force against the back surface 12 of the conically-faced head 10 and the inner lateral surface 13 of peripheral interior boss 14 at the vessel end of sleeve 15.

The valve also includes means for providing a fluid seal within the bore 8 between body 2 and the conically-faced head 10. A means for providing such seal includes O-ring 17 which is held in place between inner lateral surface 18 of peripheral interior boss 19 and sleeve 15. Spring 11 urges the stem toward the sample end of the valve such that conical face 20 of the conically-faced head 10 is urged into sealing contact with O-ring 17. Also included in the sealing means is edge 21 defined by the circular bore through surface 18 which provides a circular internal peripheral surface within the bore capable of forming a fluid seal when contacted with conical face 20. The metal-to-metal contact of edge 21 and conical face 20 has been found to provide an exceptionally efficient seal in those cases where O-ring 17 has not provided a functional seal, for instance because of deterioration or excessive internal pressure. This metal to-metal contacting seal is surprisingly efficient when compared with the devices of the prior art which utilize a spherical shaped head. To provide such sealing the angle between opposing radials in the conical face is most frequently less than 90°. A convenient angle with which excellent sealing has been demonstrated is 45°.

Figure 2:
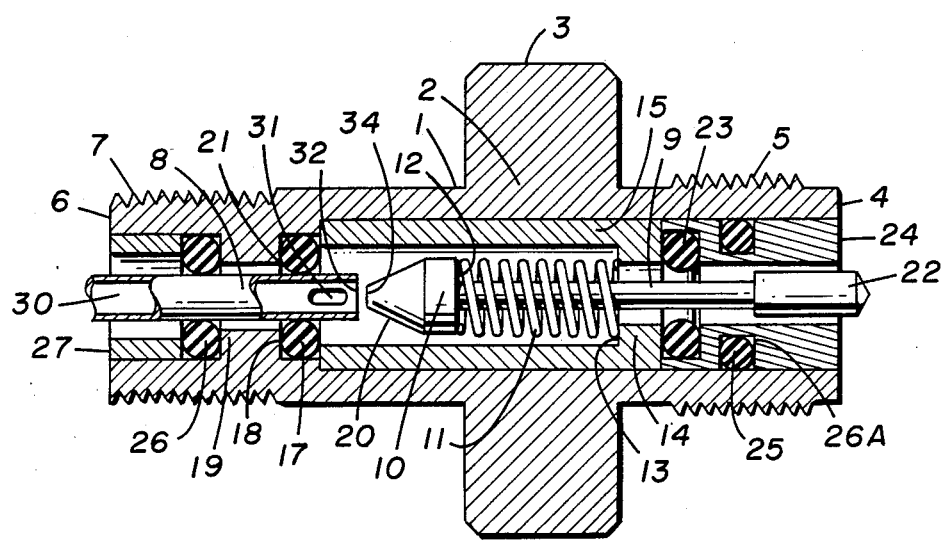

The valve stem 9 further comprises at its end proximate to the vessel end of the valve an enlarged cylindrical head 22 which assists in supplying means for providing a fluid seal within the bore between the valve stem and the body of the valve will be described in more detail with reference to FIG. 2. Such fluid seal is provided by O-ring 23 contacting the surface of cylindrical head 22. O-ring 23 is secured between the boss 14 of sleeve 15 and a recess provided at the interior end of sleeve 24. Sleeve 24 is desirably tightly fitting within the body of the valve to assist in securely holding the other internal parts of the valve in place. It is often desirable to avoid having fluids bypass the sealing systems within the valve by providing an O-ring 25 in an external peripheral slot 26 of sleeve 24.

The body of the valve also is provided at its sample end with means for receiving a hollow cylindrical sampling probe of a diameter less than the diameter provided by the bore at boss 19. Such diameter is provided through the bore to the sample end 6 of the valve by resilient O-ring 26 and O-ring retaining sleeve 27.

The operation of the valve according to this invention is described with reference to FIG. 2 which illustrates the configuration of the valve of FIG. 1 after the insertion of a hollow cylindrical sampling probe 30 into the sample end 6 of the valve. Not shown, but forming a functional part of the sample receiving system would be a stop to limit the penetration of the probe into the valve to essentially the position as illustrated in FIG. 2 are means for providing fluid communication from the probe to a fluid sample container. Aside from probe 30, all other parts of FIG. 2 correspond to those numerically identified in the above description with regard to FIG. 1.

At the fluid receiving end of probe 30 there is shown aperture 31 in the sidewall of the probe to provide fluid communication from the bore of the valve to the interior of the probe. Such aperture is advantageously provided when the otherwise open end 32 of probe 30 is occluded by the end of the conically-faced head 10 thereby restricting the flow through open end 32. In many instances it has been convenient to construct probe 30 in the form of what is commonly recognized as an air inflation needle, e.g. as is used to inflate basketballs and the like.

Because of the aperture 31 in probe 30 the need for O-ring 26 becomes apparent. O-rings 17 and 26 are selected of a diameter that will provide a fluid seal around the peripheral external surface of probe 30. As probe 30 contacts the truncated face 34 and urges stem 9 away from its fluid sealing relationship with O-ring 17 and/or edge 21, the open end of the probe 32 and aperture 31 will straddle the sealing contact made by O-ring 17, thereby allowing high pressure fluid to vent from aperture 31. Fluid leakage from aperture 31 is prevented by having O-ring 26 located at a distance form O-ring 17 at least as great as the extreme distance of aperture 31 from the end of the probe. In many cases the opening in the sidewall of the probe is at a distance from the end of the probe of less than about 3 times the outer diameter of the probe which corresponds closely to the inner diameter of the O-rings. In such cases fluid leakage from the opening in the sidewall of the hollow cylin-drical sampling probe is prevented by providing the two O-rings spaced apart in the bore by a distance of at least about 3 times the interior diameter of said O-rings.

As probe 30 is inserted into the valve and urges to the stem 9 compress axially against spring 11, enlarged cylindrical head 22 slidably disengages from sealing contact with O-ring 23 thereby allowing fluid flow between O-ring 23 and the narrower section of the stem and ultimately through the bore into the sampling probe.

O-rings utilized in the valve of this invention should be selected so as to be compatible with the fluids to be sampled.

While the invention has been described herein with regard to certain specific embodiments, it is not so limited. It is to be understood that variations and modifications thereof may be made by those skilled in the art without departing from the spirit and scope of the invention.

What is claimed is:

1. A valve comprising:
   (a) a body having one end adapted to be connected to a fluid containing vessel and a sample end adapted to be removably sealed with a cap, wherein said sample end is structured to receive a hollow cylindrical sampling probe and wherein said body has a central bore interconnecting said sample end and said other end,
   (b) within said central bore, a cylindrical valve stem having proximate to said sample end a conically-faced head and proximate to said other end an enlarged cylindrical head,
   (c) means for providing a fluid seal within said bore between said body and said conically-faced head comprising a surface substantially perpendicular to the axis of the stem, said surface having a circular bore substantially in alignment with the axis of the stem wherein said conically-faced head will not pass through said bore,
   (d) means for providing a fluid seal within said bore between said body and said cylindrical head comprising an elastomeric O-ring,
   (e) at least two elastomeric O-rings located in said bore for providing a fluid seal during insertion of a hollow cylindrical sampling probe into the valve at said sample end, and
   (f) means for biasing said valve stem to provide sealing contact against said conically-faced head and slideable sealing contact with said cylindrical head.

2. The valve of claim 1 wherein said conical head is truncated conical.

3. The valve of claim 1 where said means for providing a fluid seal between said body and said conically-faced head comprises a circular internal peripheral surface of said bore.

4. The valve of claim 1 wherein said at least two O-rings are spaced apart in said bore by a distance of at least about three times the interior diameter of said O-rings thereby preventing fluid leakage from a hollow cylindrical sampling probe having an opening in the side wall of said probe at a distance from the end of said probe of less than about three times the outer diameter of said probe.

* * * * *